(12) United States Patent
Hemmendorff

(10) Patent No.: US 7,489,760 B2
(45) Date of Patent: Feb. 10, 2009

(54) METHOD AND ARRANGEMENT RELATING TO X-RAY IMAGING

(75) Inventor: Magnus Hemmendorff, Arsta (SE)

(73) Assignee: Sectra Mamea AB, Kista (SE)

( * ) Notice: Subject to any disclaimer, the term of this patent is extended or adjusted under 35 U.S.C. 154(b) by 368 days.

(21) Appl. No.: 11/161,245

(22) Filed: Jul. 27, 2005

(65) Prior Publication Data

US 2007/0025503 A1    Feb. 1, 2007

(51) Int. Cl.
*A61B 6/04* (2006.01)
*G01N 23/04* (2006.01)

(52) U.S. Cl. .......................................... 378/37; 378/62

(58) Field of Classification Search ................ 378/4, 378/19, 20, 37, 51, 62, 98.8, 208; 382/128–132
See application file for complete search history.

(56) References Cited

U.S. PATENT DOCUMENTS

| | | | |
|---|---|---|---|
| 7,245,694 B2 * | 7/2007 | Jing et al. | 378/37 |
| 7,298,876 B1 * | 11/2007 | Marshall et al. | 382/128 |
| 7,309,867 B2 * | 12/2007 | Costa et al. | 250/458.1 |

* cited by examiner

*Primary Examiner*—Irakli Kiknadze
(74) *Attorney, Agent, or Firm*—Novak Druce + Quigg LLP

(57) ABSTRACT

Methods and arrangement for providing digital x-ray mammography image acquisition by means of an X-ray system that includes acquiring image data by irradiating an object, such as a human breast, automatically by the system analyzing the acquired image data with respect to presence of motion blur, indicating whether motion blur is present.

57 Claims, 15 Drawing Sheets

METHOD AND ARRANGEMENT RELATING TO X-RAY IMAGING

TECHNICAL FIELD OF THE INVENTION

The present invention relates to a method and arrangement in X-ray mammography imaging, and in particular scanning systems and image processing.

BACKGROUND OF THE INVENTION

Motion blur may degrade image quality, in particular for X-ray mammography where images have to be very sharp to see small micro-calcifications.

In a typical workflow of screening mammography, patients leave the clinic before the images are thoroughly reviewed. When the motion blur is discovered, patients may have to be called back to acquire new images, which may cause inconvenience, anxiety and additional expenses. Normally, the "motion blur" origins from the small displacements of the patient's movements.

Efficient workflow is very important for specialized screening mammography clinics where healthy patients are examined on a regular basis. Speed requirements and cost control have driven many clinics to introduce a workflow that resembles an assembly line. Thus, the demands and requirements for mammography systems are different compared to other applications of medical X-ray imaging.

FIG. 1 illustrates a known configuration for an X-ray imaging system that scans a breast and acquires a set of overlapping part images, and computes a resultant image from said part images. The part images arise from irradiation of a human breast using a bundle of X-ray beams. Said bundle of beams is created by an X-ray source 110 and a collimator 120 with a set of long narrow apertures, also referred to a slits. Each slit forms a thin X-ray beam, which irradiates the imaged breast and rays passing through are received by a photon counting line detector. There is one line detector for each slit, mounted in a common detector unit 150.

In Ph.D. thesis "Motion Estimation and Compensation in Medical Imaging" by Magnus Hemmendorff, Linköping Studies in Science and Technology, dissertations thesis No. 703, Jul. 2001, hereby expressly incorporated by reference in its entirety, methods for generation of local motion constraints are described. One method is based on phase from quadrature filters; another is based on canonical correlation and scalar products of quadrature filters. In both methods, a local confidence measure is produced to increase accuracy and robustness. The local phase variations are used to generate local motion constraints and a motion field can be estimated by least square fit of parametric motion models, such as shift models, affine models and finite element models.

SUMMARY OF THE INVENTION

At least one object of the present invention is to provide a digital x-ray mammography system and method that assures the obtaining of an image free from motion blur without recalls and with minimal costs and inconvenience. An aspect is to detect whether or not motion blur is present. Another aspect is to do a retake in the case where motion blur is present, and the retake may be assisted by an automatic workflow. Yet another aspect of the invention relates to automatic correction of already acquired data.

Thus, a method of detection and correction of motion blur in the resultant image is presented. For a mere detection, the resultant image may be analyzed with respect to blur, but preferably, the part images are compared with respect to alignment, which also allows correction.

One aspect of the invention is providing warnings in case motions have been detected and instructing in the user or an automatic workflow controller to review the acquired image or to make a retake of a new image and the system is automatically put in a state to acquire the image again. To speed up a retake, the system may automatically set up the same parameters again. Preferably, the apparatus should once again be mechanically adjusted to fit the patient's left or right breast in the same angle and repeat the instructions for image acquisition. The same exposure parameters may be used again and the images should get the appropriate labels. Depending on configuration, the system may discard the blurred image or keep it with special information that can later be used to prevent a radiologist from spending much time reviewing a blurred image.

According to a first aspect, a method for digital x-ray mammography image acquisition by means of an X-ray system is presented as illustrated in FIG. 14, the method comprises (includes, but is not necessarily limited thereto): acquiring image data by irradiating a human breast, automatically by said system analyzing said acquired image data with respect to presence of motion blur, and indicating whether motion blur is present. In one embodiment, the user is notified whether blur is present. A computer may control a workflow with respect to which an image is acquired and said workflow automatically depends on whether blur is present or not. The computer automatically sets parameters for image acquisition, and in case of retake, the system automatically sets a combination parameters that are special for the view, being one or several of a left or right breast, irradiation angle, positioning message to the user, or information to be stored together with the retaken image. Presence of motion blur is indicated if a set of pre-defined image parameters exceed a threshold, and said image parameters are computed from said image data. The image parameters comprise statistics of sharpness of image contours. The acquired image data comprises a set of partly or fully overlapping part images. The overlapping portions of said part images are a temporal sequence of images. The method may be based on a multi-slit scanning technology, and overlapping part images being from different slits. The image parameters are computed from comparative analysis with respect to alignment, and comparison of data derived from essentially different sets of part images. The calculation of the image parameters involves estimation of motion vectors, components of motion vectors or cost functions of parameters for displacement. The comparative analysis comprises computation of statistics of dissimilarity due to motions. The indication is presented as a message suggesting that image quality should be reviewed and/or image should be retaken.

According to a second aspect of the invention, illustrated in FIG. 15, a method in digital x-ray mammography acquisition is presented comprising: acquiring image data by irradiating a human breast using a bundle of x-ray beams that scan an examination area containing said breast, producing a set of overlapping part images, automatically by said system analyzing said overlapping part images with respect to motions, indicating whether motions, or motion blur is present. The method further comprises presenting presence of a motion to a user.

According to the method, a decision or suggestion is made automatically which image to acquire, and said decision or suggestion depends on whether or not motions are present. According to the method motions are corrected by aligning said part images, in case motion is present. The presence of motion blur is determined by exceeding a threshold value in predetermined image parameters in the sequence of said overlapping part images. The image parameters are computed using comparative analysis of part images, to detect systematic variations. The method further comprises estimation of motion along at least one spatial direction, or motion constraints or cost functions for motion vectors. The motion estimation involves spatial gradients and temporal differences or derivatives of images derived from said part images.

According to a third aspect of the invention, a method for digital x-ray mammography image acquisition is presented, illustrated in FIG. 16, comprising: acquisition of a set of substantially overlapping part images by irradiating a human breast using X-rays, fine-alignment of said part images based on their contents, construction of a corrected resultant image by merging said part images. The source of the part images is separate thin x-ray beams arranged in a bundle that scan the examination area. The part images are from a detector producing multiple readouts in a temporal sequence, where said part images form a temporal sequence of partly or fully overlapping part images. The alignment is based on estimation of local vectors that describe motion or displacements. The estimation of motions involve spatial and temporal gradients or phase from either quadrature filters, Gabor filters, Fourier transforms or Hilbert transforms. The motion estimation is based on finite element models or least squares fit of parametric motion models. The alignment is based on an image registration algorithm.

According to a fourth aspect of the invention, as illustrated in FIG. 17, a method for digital x-ray mammography image acquisition comprising: acquisition of a set of substantially overlapping part images by scanning an examination field using a set of x-ray beams arranged in a bundle, fine-alignment of said overlapping part images based on contents of said part images, construction of a resultant image based on said part images. The method further comprises reducing motion blur in said resultant image through said alignment based on the contents of the part images. The alignment is based on image registration. The image registration computes its parameters based on pre-merged part images or image data derived from multiple part images. The fine-alignment is based on estimation of motion vectors, which are used to correct said part images. The motion estimation involves spatial gradients and temporal derivatives. The estimation of motions involves phase from either quadrature filters, Gabor filters, Fourier transforms or Hilbert transforms. The estimation of motions involves one or several of finite element methods or least square fit of parametric motion models. The estimation of motions involves finite element methods, which are adapted to a scanning geometry, such as distance between slits measured in the pixel domain.

The invention relates to a digital x-ray mammography system comprising an x-ray source, a detector and means for receiving an object to be examined, said detector being arranged to produce a signal corresponding to the exposure of said object to x-rays passing through said object, and means for generating an image data, said system further comprising an arrangement for automatically analyzing said image data with respect to presence of motion blur. The system further comprises means for indicating presence of motion blur. The system further comprises a computer for controlling a workflow with respect to which an image is acquired, said workflow automatically depending on whether blur is present or not. The computer is operatively arranged to automatically set parameters for image acquisition, said parameters being set automatically that are special for a retake. The system further comprises means for detecting presence of a motion blur by monitoring exceed of a threshold value. The acquired image data comprises a set of partly or fully overlapping part images. The system comprises a multi-slit scanning technology, and overlapping part images being from different slits. The system may comprise means for computing said image parameters from comparative analysis with respect to alignment, and comparison of data derived from essentially different sets of part images. The calculation of said image parameters involves estimation of motion vectors, components of motion vectors or cost functions of parameters for displacement. The comparative analysis comprises computing statistics of dissimilarity due to motions. The system comprises a presentation device for presenting said indication as a message suggesting that image quality should be reviewed and/or image should be retaken.

The invention also relates to a digital x-ray mammography system comprising an x-ray source, a detector and means for receiving an object to be examined, said detector being arranged to produce a signal corresponding to the exposure of said object to x-rays passing through said object, and means for generating an image data and acquisition of a set of substantially overlapping part images by scanning an examination field using a bundle of x-ray beams from said x-ray source, an arrangement for fine-alignment of said overlapping part images based on contents of said part images, and an arrangement for constructing a resultant image based on said part images.

The invention also relates to an arrangement in a digital x-ray mammography apparatus for image correction, the arrangement comprising a displacement estimator, displace/warp units and an image merger. The image merger is a mean value calculator. The x-ray apparatus is of multi-slit type and said displacement estimator and controller is arranged to receive image data from a detector for each slit and estimate the displacement based on comparison of part images to each other or to a reference image derived from multiple part images. The arrangement comprises an arrangement comprising a threshold for motion detection, which computes an overall figure of merit of estimated motions and compares to a pre-defined threshold value. The estimator comprises instructions for estimation of motion vectors, said instructions being one or several of: a block matching algorithms that search for maximum correlation/similarity or minimal difference of relatively displaced blocks, instructions for finding correspondence for selected features, such as corners or edges, gradient algorithms for optical flow, that use derivatives of the image in spatial and temporal directions to locally estimate one component of the motion vector, phase from Gabor filters, or quadrature Filters, or Fourier transforms, parametric motion models or finite element methods.

The invention also relates to a computer program stored on a memory for digital x-ray mammography image acquisition by means of an X-ray system, the computer program comprising: an instruction set for acquiring image data by irradiating an object, an instruction set for automatically analyzing said acquired image data with respect to presence of motion blur, and an instruction set for indicating whether motion blur is present.

The invention also relates to a computer program stored on a memory for digital x-ray mammography acquisition comprising; an instruction set for acquiring image data by irradiating an object using a bundle of x-ray beams that scan an examination area containing said object, an instruction set for producing a set of overlapping part images, and an instruction set for analyzing said overlapping part images with respect to motions, and an instruction set for indicating whether motions, or motion blur is present.

The invention also relates to a computer program stored on a memory for digital mammography x-ray image acquisition comprising: an instruction set for acquisition of a set of substantially overlapping part images by scanning an examination field using a set of x-ray beams arranged in a bundle, an instruction set for fine-alignment of said overlapping part images based on contents of said part images, and instructions for construction of a resultant image based on said part images.

BRIEF DESCRIPTION OF THE DRAWINGS

In the following, the invention will be further described in a non-limiting way with reference to the accompanying drawings in which.

DETAILED DESCRIPTION OF THE EMBODIMENTS

The invention relates to digital x-ray mammography image acquisition, detection and correction in general and in particular systems where image data is integrated over time, such as multi-slit scanners.

Figure 1:
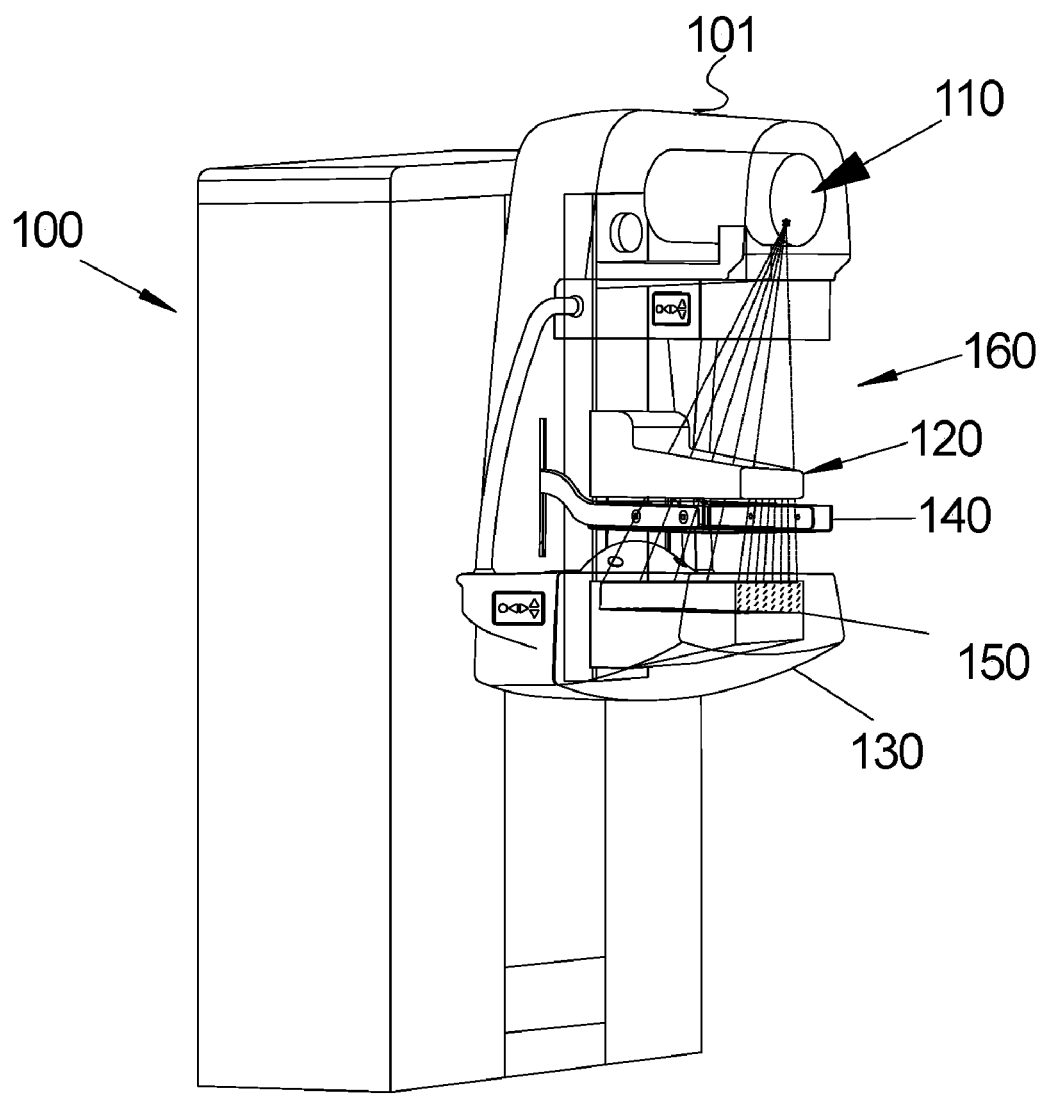
FIG. 1 is a perspective, schematic illustration of an exemplary scanning multi-slit digital X-ray imaging apparatus of known design.
Figure 2:
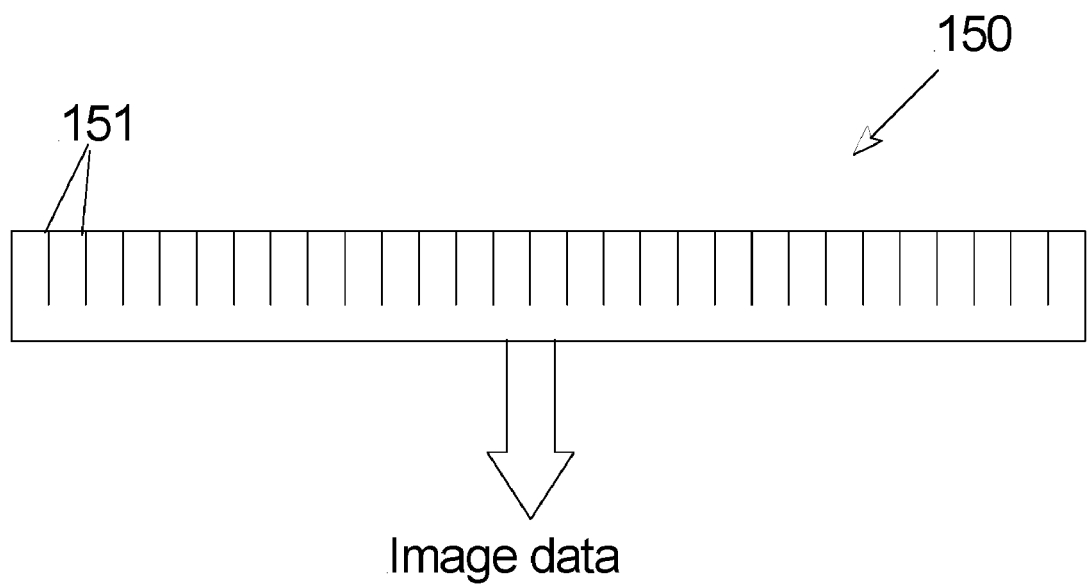
FIG. 2 is a schematic view of a photon detector used in one embodiment of the invention.
Figure 3:
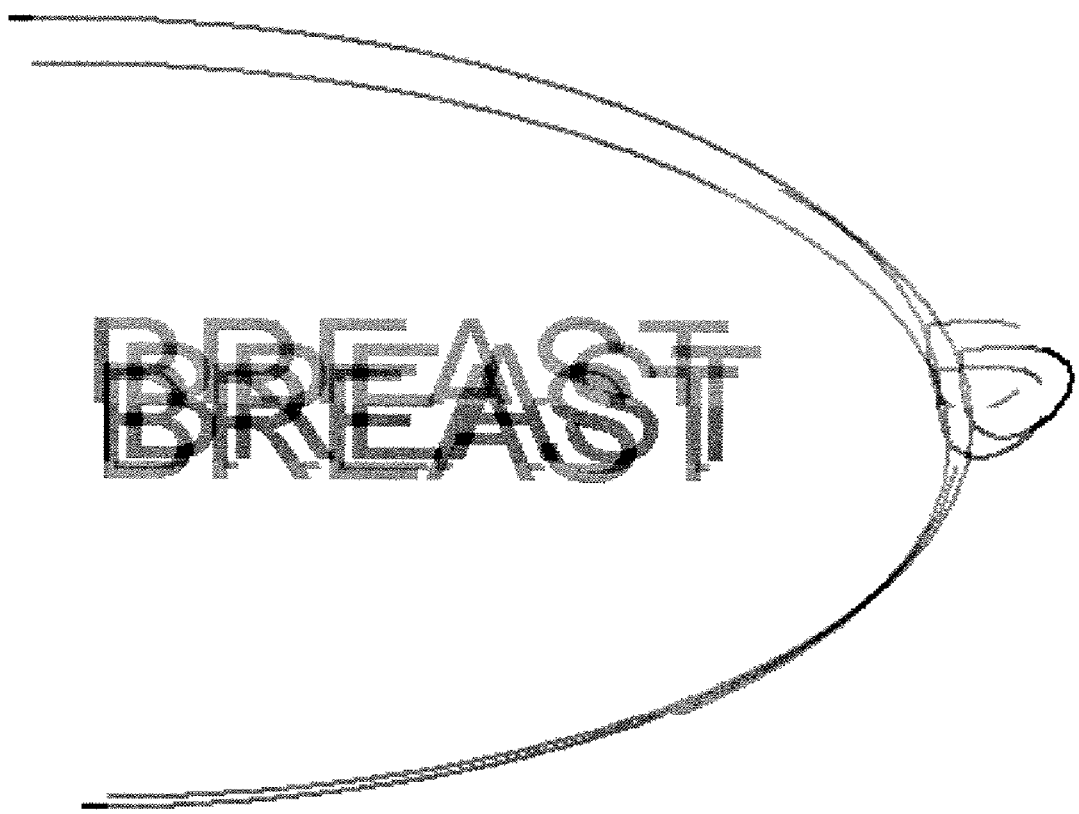
FIG. 3 is a schematic motion blurred view of an examined object.

FIG. 2 illustrates a part of an exemplary photon detector 150 having twenty eight (28) pixel lines 151, i.e. 28 line detectors. Each line detector is a silicon strip with a multiple of 768 channels, (but individual channels are too small to be illustrated). Each line detector receives photons from one thin x-ray beam, formed by a slit in the collimator. According to this example, the resulting detector output is 28 overlapping part images. The detector assembly moves essentially perpendicular to the detector lines and multiple detector lines collect image data from essentially the same image area. Different slits and detector lines pass the same point in the image field at different instants of time. If the imaged object moves during that time interval, the images from different slits will not match as expected. A resulting image of a moving breast of an examined patient is illustrated in FIG. 3. Unlike this simplified example, the typical motion is small, just a few pixels, but nevertheless it degrades image quality. Another difference is that motions are non-uniform and the motions vectors vary over the image.

Figure 4:
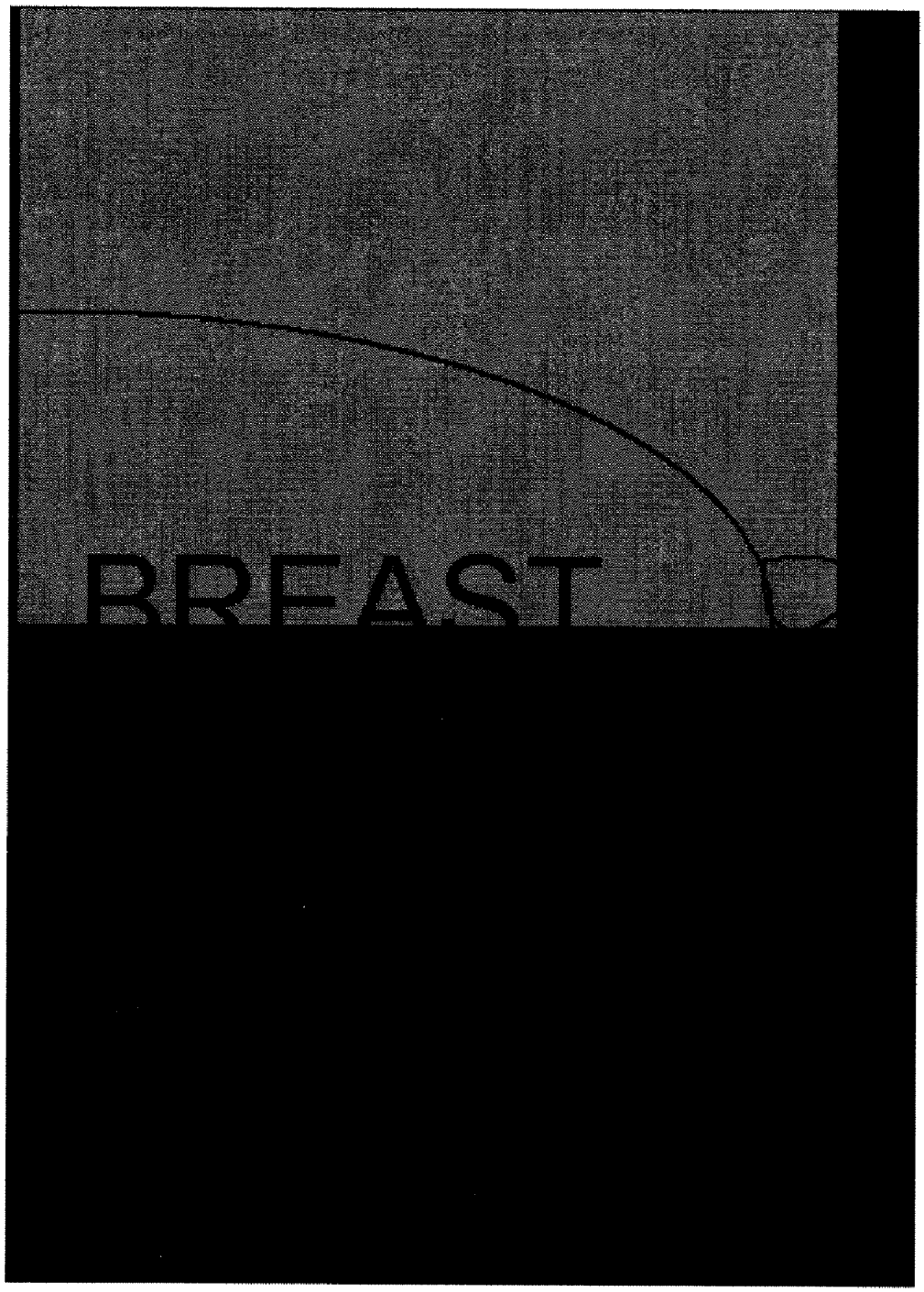
FIGS. 4 to 7 illustrate a sequence of sums of 1, 2, 3 and 4 overlapping part images, and resulting blur due to motions.
Figure 5:
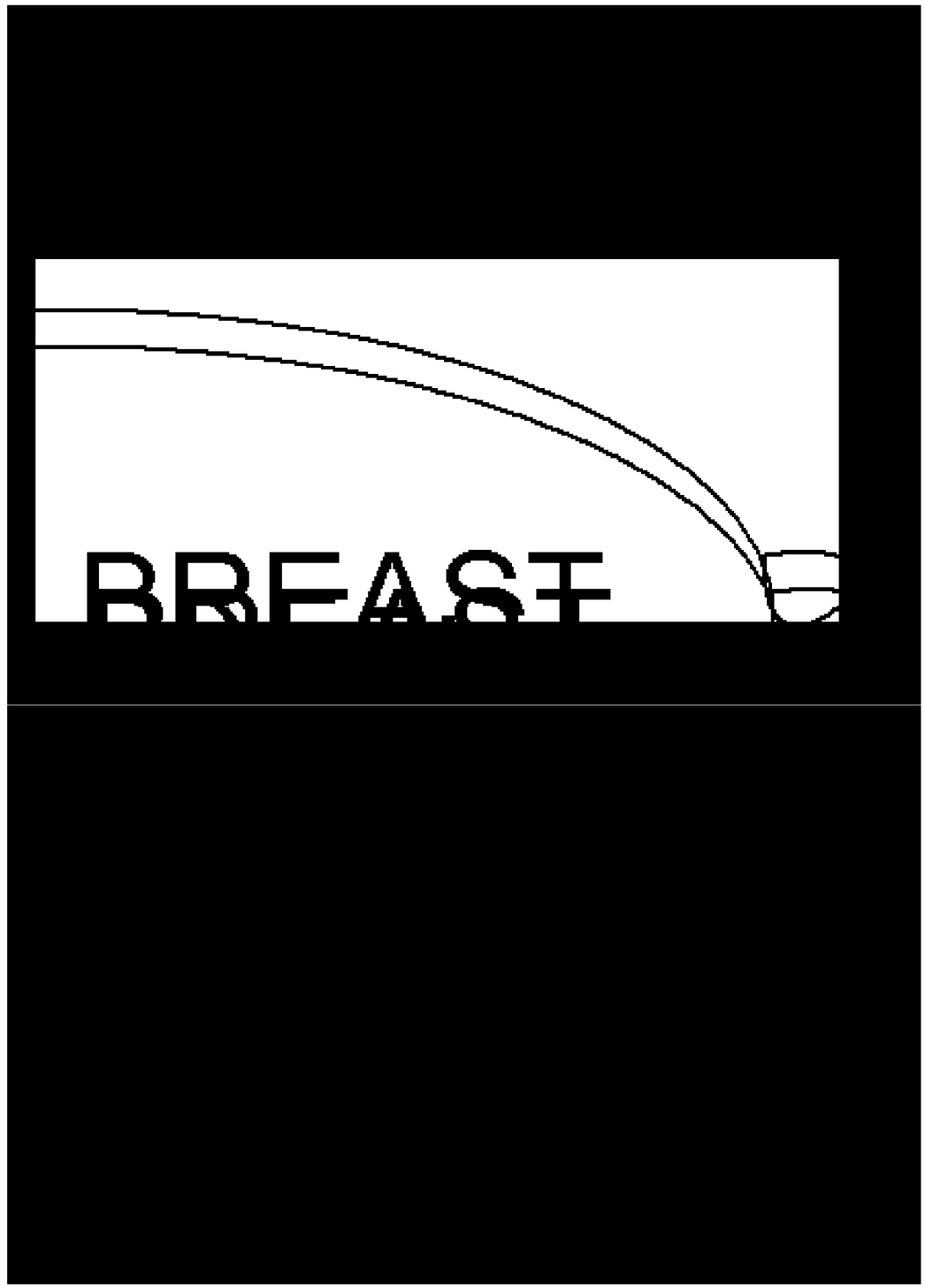
Figure 6:
Figure 7:
Figure 8:
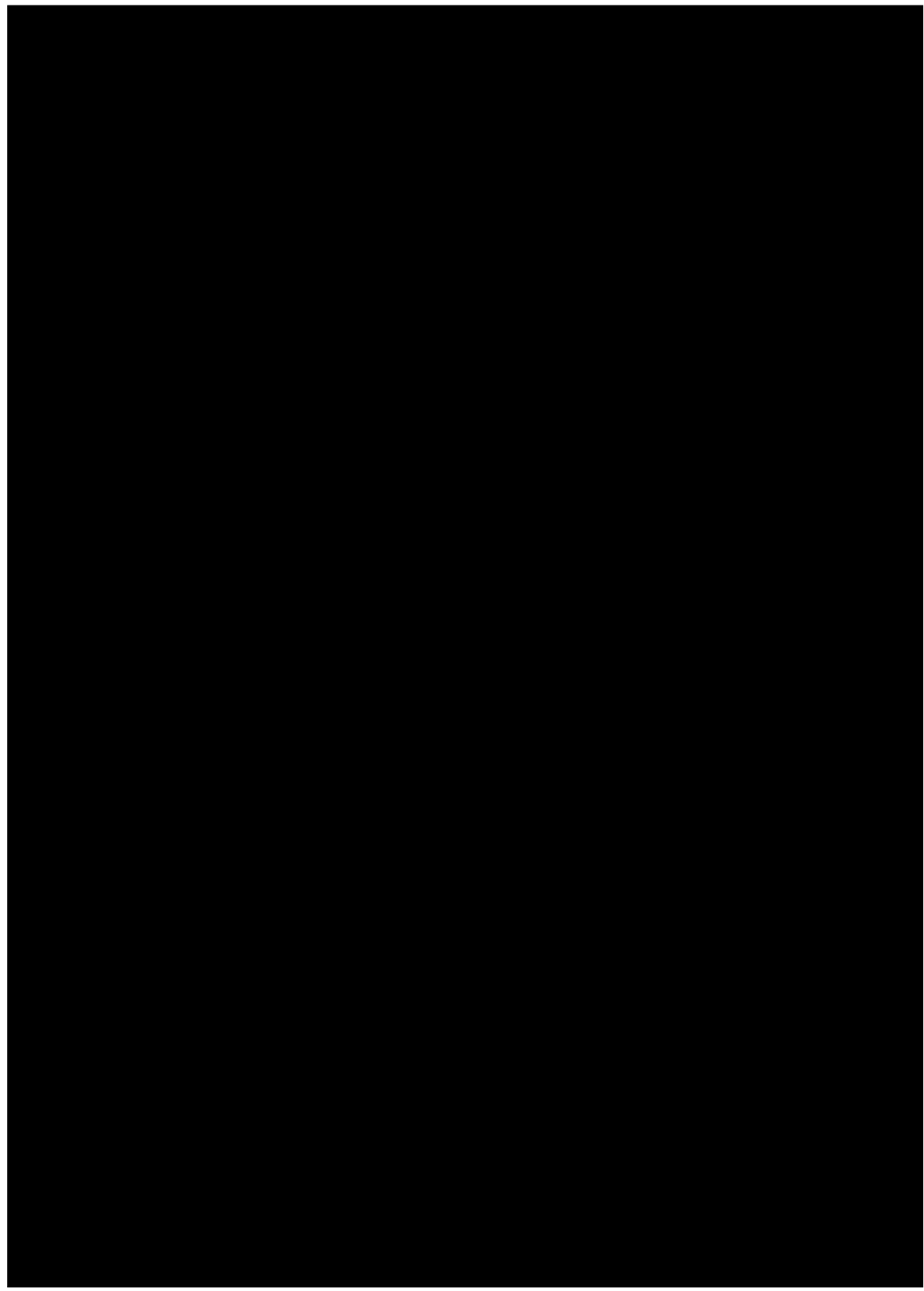
FIGS. 8 to 11 illustrate the sum of aligned or corrected part images from FIGS. 4 to 7 blur-free.
Figure 9:
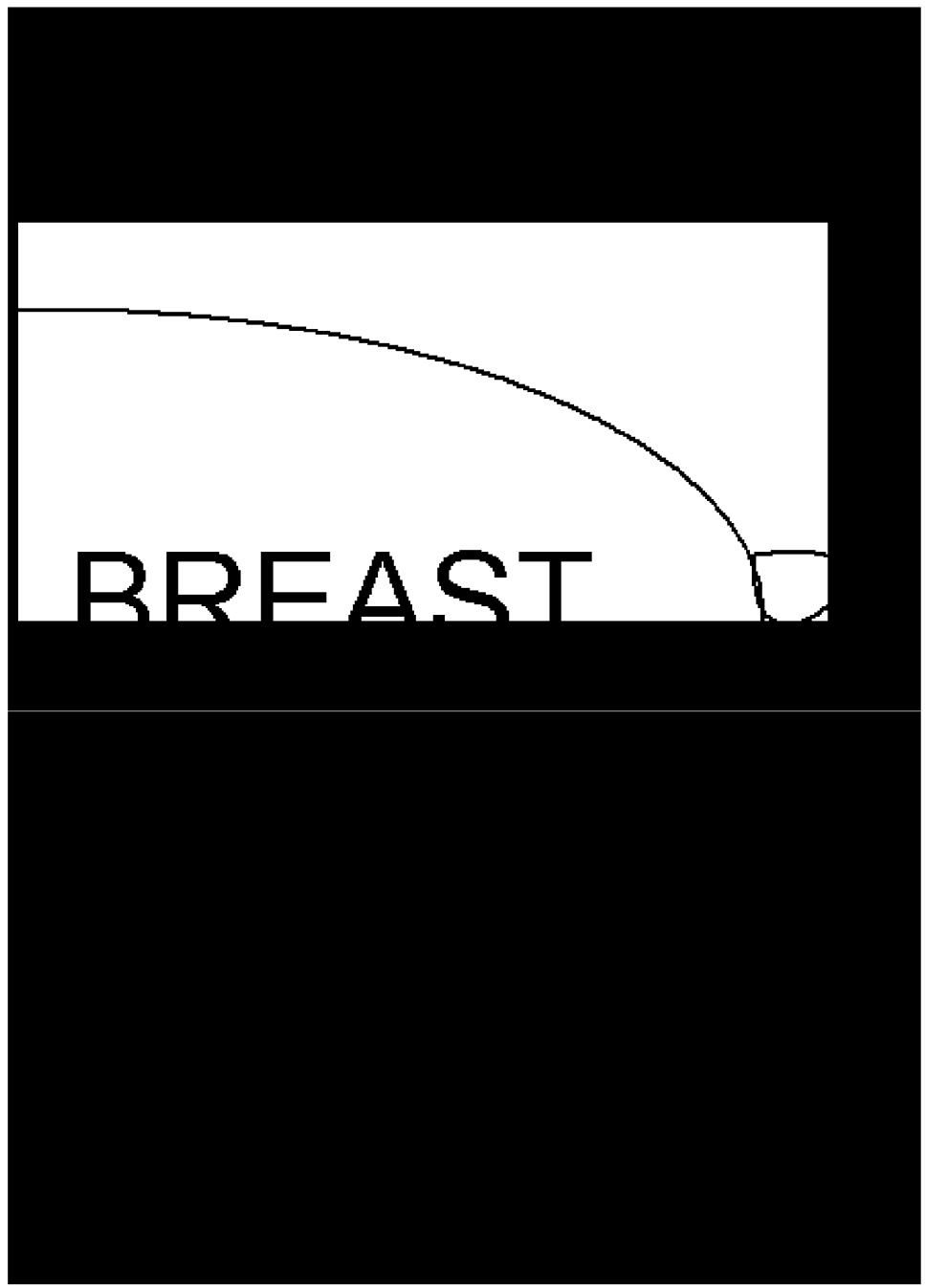
Figure 10:
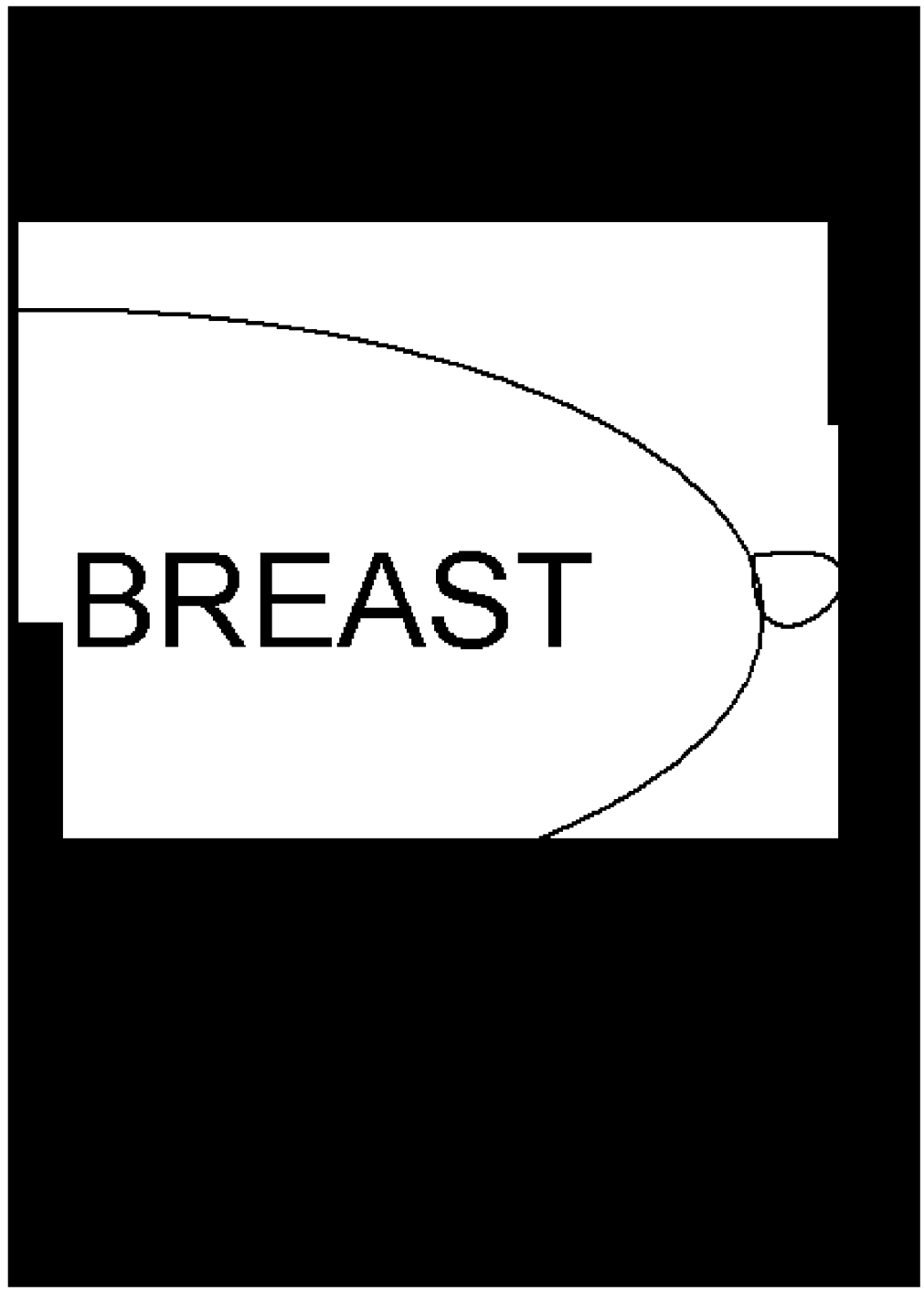
Figure 11:
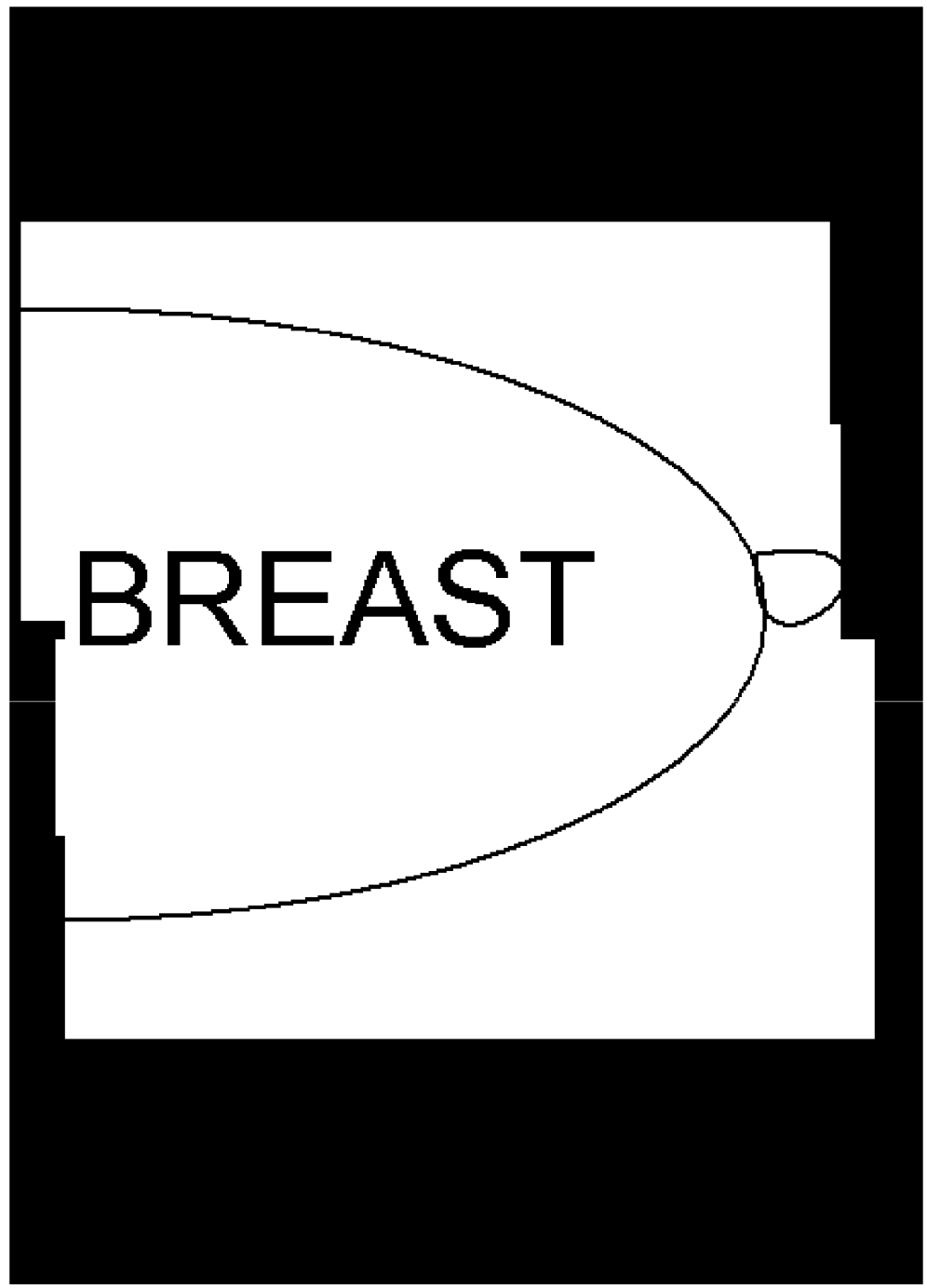

FIG. 4 illustrates the first part image received from one detector line, where the scan direction is downwards, with respect to the plane of the drawing. FIG. 5 illustrates the sum of the first two part images in the sequence. FIGS. 6 and 7 illustrate the effect of more overlapping image parts. Due to the motions, the image quality is degraded. The overlaps are due to the fact that each slit of the collimator acquires a part image, and the slit-images are partly overlapping. Disregarding noise and other imperfections, these overlapping parts of the slit-images are supposed to be identical, but they are relatively displaced due to motion of the object relative to the imaging device. The other imperfections may be fluctuations in detector efficiency, lack of calibration, unequal slit width, X-ray output and individual detector sensitivity. Such imperfections increase the level of difficulty for automatic alignment algorithms, and call for robust methods such as phase-based methods.

FIGS. 8 to 11 illustrate same sequence as previously (FIGS. 3-7), but this time the part images are perfectly aligned.

The preferred embodiment estimates motion vectors in order to detect and correct motion blur. For mere motion detection, it is however possible to skip explicit computation of motion vectors. In one embodiment, it is enough to use a gauge of the overall abundance of motions, and estimate their impact on the image quality. The motion vectors are estimated comprising local offset, shift, rotation, deformation, and position relative data from different part images is conducted. A motion detecting system presents a warning when the motion vectors as a whole, weighted based on image contents, exceed a set of pre-defined threshold. Correction uses the estimated motion vectors to warp, i.e. shift, move or resample the part images so that alignment is improved. The aligned part images are merged pixel-wise to form a corrected resultant image. In the preferred embodiment, the resultant image is constructed by computing the average of all overlapping part images for each pixel, i.e. computing the sum and dividing by the number of contributing part images in each pixel. However, averaging is not the only useful method of merging data. The optimal method depends on the kind of noise distribution in the part images, which in turn depends on the photon detector. For example, median may be better than averaging if the part images are contaminated by outliers or so called "salt and pepper" noise. A middle way is outlier rejection followed by averaging.

Figure 13:
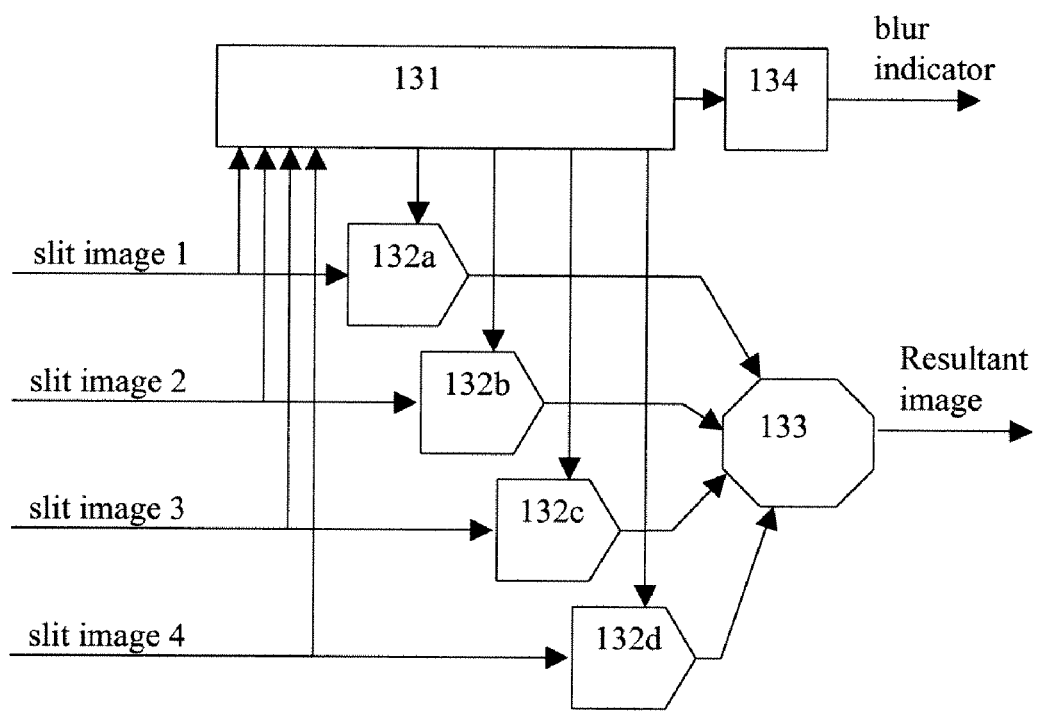
FIG. 13 illustrates an exemplary block diagram for estimation, correction and image construction for a multi-slit system.
Figure 14:
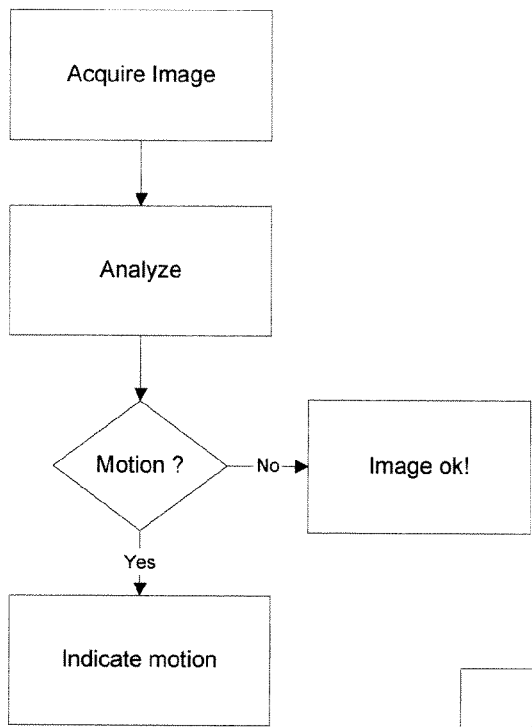
FIG. 14 illustrates a flow diagram of a method for motion detection according to a first aspect of the invention.
Figure 15:
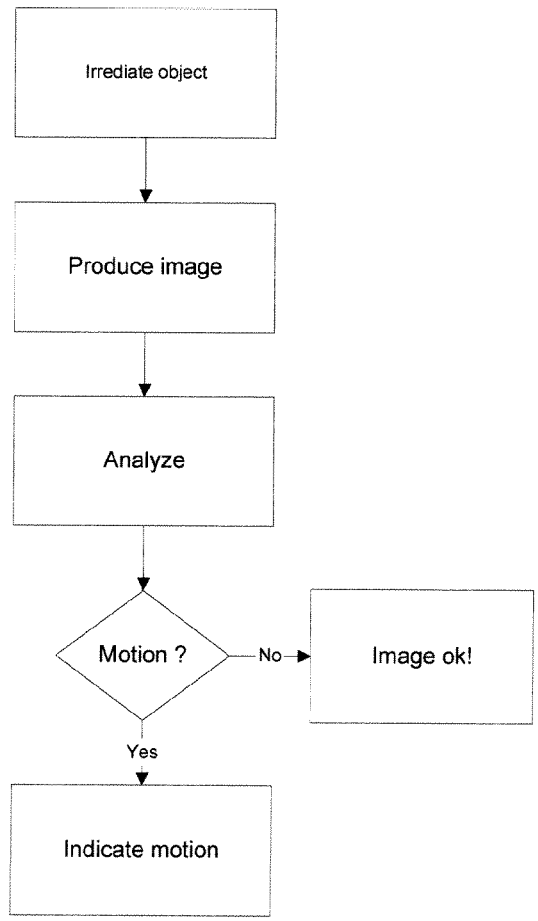
FIG. 15 illustrates a flow diagram of a method for motion detection according to a second aspect of the invention.
Figure 16:
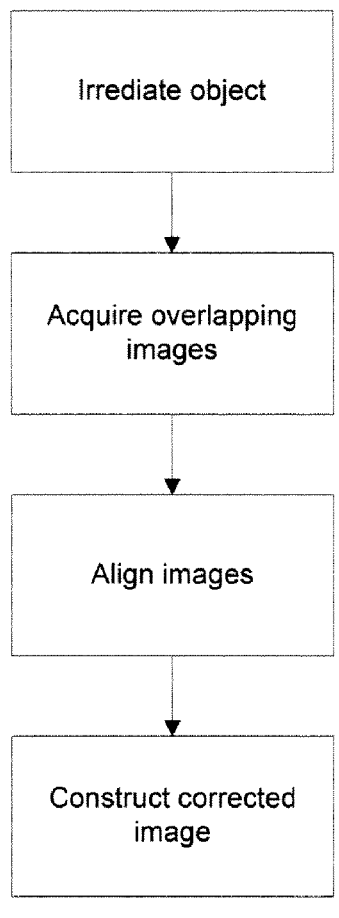
FIG. 16 illustrates a flow diagram of a method for motion detection according to a third aspect of the invention.
Figure 17:
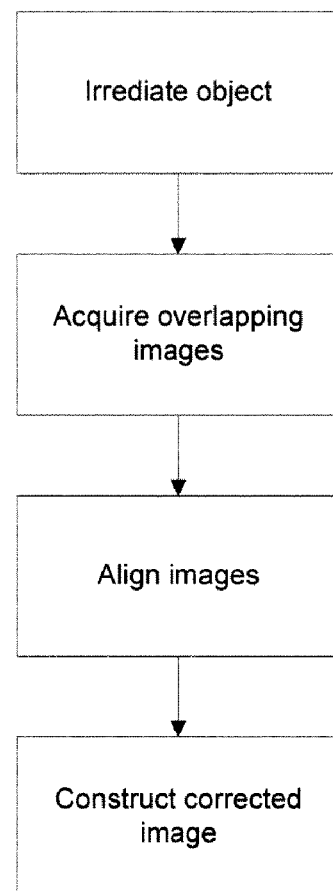
FIG. 17 illustrates a flow diagram of a method for motion detection according to a fourth aspect of the invention.

FIG. 13 illustrates an exemplary arrangement for image correction according to present invention. The arrangement is used for estimation, correction and image construction for a multi-slit system. The arrangement comprises a displacement estimator 131, displace/warp units 132a-132d (depending on the number of slits) and an image merger 133, which is normally a mean value calculator. The displacement estimator 131 and controller receives image data from the detector for each slit (four in this case) and estimate the displacement based on comparison of part images to each other or to a reference image derived from multiple part images. 134 contains a threshold for motion detection, which computes an overall figure of merit of estimated motions and compares to a pre-defined threshold value.

Algorithms for estimation of motion vectors in 131 may be virtually any algorithm for image registration, image fusion or motion estimation, for example:

Block matching algorithms that search for maximum correlation/similarity or minimal difference of relatively displaced blocks.

Finding correspondence for selected features, such as corners or edges.

Gradient Algorithms for optical flow, that use derivatives of the image in spatial and temporal directions (x, y, t) to locally estimate one component of the motion vector, based on a famous publication by Horn & Schunk, 1981.

Phase from Gabor filters, or quadrature Filters, or Fourier transforms, e.g. Fleet and Jepson, Hemmendorff 1997, 1999 and 2002.

Parametric motion models or finite element methods.

In the preferred embodiment, a two-step algorithm is used. The first step is estimation of local descriptors of the local motions, commonly referred to as gradient constraints, motions constraints, motion tensors or local cost functions. The local descriptors are estimated using phase from quadrature filters. The second step is least square fitting of local motion vectors to said motion constraints. To produce reliable motion vectors in image parts with noise and without sufficient contours, the process involves use of motion descriptors at other image coordinates. This is achieved using global parametric models, such as affine models, quadratic models or finite element models with stiffness matrices or cost functions on deformations. In this case a spatiotemporal finite element model is implemented, where coordinates span both location and time or slit number, based on accurate information about scanning geometry in the pixel domain. According to commonly accepted finite element method theory, a cost function for deformations should be used, which is commonly implemented using a stiffness matrix. Every element in the finite element model gets a cost function based on its motion relative to nearby elements. The first version of our preferred implementation uses a simpler and computationally faster method can be to low-pass filter descriptors across the image and then solve the motion in least squares sense. Said descriptors are outer products of motion constraint vectors or, or the matrices and vectors of contributions from local parametric motion models. This method is equivalent to fitting local motion vectors in overlapping image regions. The low-pass filtering can also be spatio-temporal and filter descriptors across data from different slits based on a model of the detector geometry.

Figure 12:
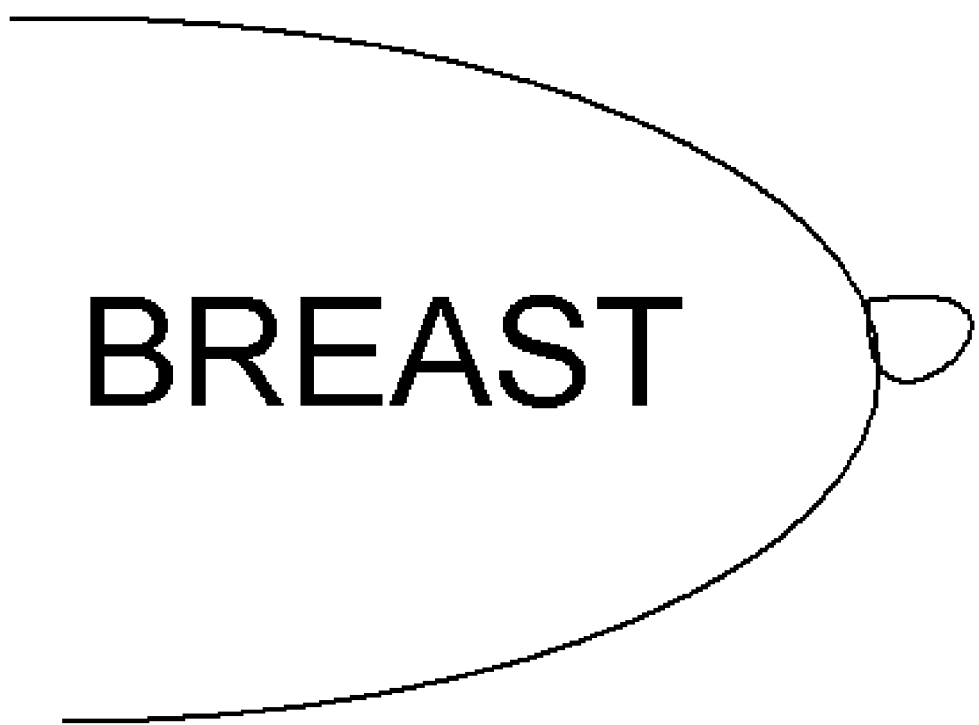
FIG. 12 illustrates a resulting image free from blur after mean value calculation of the corrected/aligned images.

The signals from the detector are also fed to a corresponding displace/warp unit 132a-132d, which also obtain parameters from the estimator 131. The parameters are typically local motion vectors, or their inverse. The output from each displace/warp unit 132a-132d is used as an input to the image merger 133, which preferably computes a mean value image of all corrected part images and outputs a corrected, sharp full-field image of the breast (FIG. 12).

The invention is not only limited to motion blur due to patient motions. The scanning device itself may also move, which also make part images mismatch. Motion-like blur may also be due to lack of accurate information about the relative position of the part images. The invention applies to all such cases, since the effect appear the same way in the image data as object motions. When describing the invention, the word motion also refers to displacement due to such reasons, since they appear as object motions in the acquired image data.

The invention may also be realized as computer program comprising procedures for executing the steps mentioned earlier.

The invention is not limited to the shown embodiments but can be varied in a number of ways without departing from the scope of the patent claims and the arrangement and the method can be implemented in various ways depending on application, functional units, needs and requirements and the like.

What is claimed is:

1. A method for digital x-ray mammography image acquisition by means of an X-ray system, the method comprising:
   a. acquiring image data by irradiating a human breast;
   b. automatically by said system analyzing said acquired image data with respect to presence of motion blur; and
   c. indicating whether motion blur is present;
   wherein said acquired image data comprises a set of partly or fully overlapping part images.

2. The method according to claim 1, wherein the user is notified whether blur is present.

3. The method according to claim 1, wherein a computer controls a workflow with respect to which an image is acquired and said workflow automatically depends on whether blur is present or not.

4. The method according to claim 3, wherein said computer automatically sets parameters for image acquisition, and in case of retake, the system automatically sets a combination of parameters that are special for the view, being one or several of a left or right breast, irradiation angle, positioning message to the user, or information to be stored together with the retaken image.

5. The method according to claim 1, wherein presence of motion blur is indicated if a set of pre-defined image parameters exceed a threshold, and said image parameters are computed from said image data.

6. The method according to claim 5, wherein said image parameters comprise statistics of sharpness of image contours.

7. The method according to claim 1, wherein the overlapping portions of said part images are a temporal sequence of images.

8. The method according to claim 1, wherein said x-ray system is a multi-slit scanning system and overlapping part images are obtained from different slits in said system.

9. The method according to claim 1, wherein said image parameters are computed from comparative analysis with respect to alignment, and comparison of data derived from essentially different sets of part images.

10. The method according to claim 9, wherein calculation of said image parameters involves estimation of motion vectors, components of motion vectors or cost functions of parameters for displacement.

11. The method according to claim 9, wherein said comparative analysis comprises computation of statistics of dissimilarity due to motions.

12. The method according to claim 1, wherein said indication is presented as a message suggesting that image quality should be reviewed and/or image should be retaken.

13. A method for digital x-ray mammography acquisition comprising:
   a. acquiring image data by irradiating a human breast using a bundle of x-ray beams that scan an examination area containing said breast, producing a set of overlapping part images;
   b. automatically by said system analyzing said overlapping part images with respect to motions; and
   c. indicating whether motions, or motion blur is present.

14. The method according to claim 13, presenting presence of a motion to a user.

15. The method according to claim 13, wherein said system automatically makes a decision or suggestion which image to acquire, and said decision or suggestion depends on whether or not motions are present.

16. The method according to claim 13, where said system corrects for motions, by aligning said part images, in case motion is present.

17. The method according to claim 16, wherein presence of motion blur is determined by exceeding a threshold value in pre-determined image parameters in the sequence of said overlapping part images.

18. The method according to claim 17, wherein said image parameters are computed using comparative analysis of part images, to detect systematic variations.

19. The method according to claim 18, comprising estimation of motion along at least one spatial direction, or motion constraints or cost functions for motion vectors.

20. The method according to claim 19, wherein motion estimation involves spatial gradients and temporal differences or derivatives of images derived from said part images.

21. A method for digital x-ray mammography image acquisition comprising:
   a. acquisition of a set of substantially overlapping part images by irradiating a human breast using X-rays;
   b. fine-alignment of said part images based on their contents; and
   c. construction of a corrected resultant image by merging said part images.

22. The method according to claim 21, wherein the source of the part images is separate thin x-ray beams arranged in a bundle that scan the examination area.

23. The method according to claim 22, wherein said alignment is based on estimation of local vectors that describe motion or displacements.

24. The method according to claim 22, wherein said alignment is based on an image registration algorithm.

25. The method according to claim 21, wherein said part images are from a detector producing multiple readouts in a temporal sequence, where said part images form a temporal sequence of partly or fully overlapping part images.

26. The method according to claim 25, wherein said alignment is based on estimation of local vectors that describe motion or displacements.

27. The method according to claim 26, wherein said estimation of motions involve spatial and temporal gradients or phase from either quadrature filters, Gabor filters, Fourier transforms or Hilbert transforms.

28. The method according to claim 26, wherein said motion estimation is based on finite element models or least squares fit of parametric motion models.

29. The method according to claim 25, wherein said alignment is based on an image registration algorithm.

30. A method for digital x-ray mammography image acquisition comprising:
   a. acquisition of a set of substantially overlapping part images by scanning an examination field using a set of x-ray beams arranged in a bundle;
   b. fine-alignment of said overlapping part images based on contents of said part images; and
   c. construction of a resultant image based on said part images.

31. The method according to claim 30, reducing motion blur in said resultant image through said alignment based on the contents of the part images.

32. The method according to claim 31, wherein said alignment is based on image registration.

33. The method according to claim 32, wherein said image registration computes its parameters based on pre-merged part images or image data derived from multiple part images.

34. The method according to claim 31, wherein said fine-alignment is based on estimation of motion vectors, which are used to correct said part images.

35. The method according to claim 34, wherein said motion estimation involves spatial gradients and temporal derivatives.

36. The method according to claim 34, wherein said estimation of motions involve phase from either quadrature filters, Gabor filters, Fourier transforms or Hilbert transforms.

37. The method according to claim 34, wherein said estimation of motions involves one or several of finite element methods or least square fit of parametric motion models.

38. The method according to claim 34, wherein said estimation of motions involves finite element methods, which are adapted to a scanning geometry, such as distance between slits measured in the pixel domain.

39. A digital x-ray mammography system comprising an x-ray source, a detector and means for receiving an object to be examined, said detector being arranged to produce a signal corresponding to the exposure of said object to x-rays passing through said object, and means for generating an image data comprising a set of partly or fully overlapping part images, said system further comprising an arrangement for automatically analyzing said image data with respect to presence of motion blur.

40. The system of claim 39 further comprising means for indicating presence of motion blur.

41. The system of claim 39 further comprising a computer for controlling a workflow with respect to which an image is acquired, said workflow automatically depending on whether blur is present or not.

42. The system of claim 41, wherein said computer is operatively arranged to automatically set parameters for image acquisition, said parameters being set automatically that are special for a retake.

43. The system of claim 39 further comprising means for detecting presence of a motion blur by monitoring exceed of a threshold value.

44. The system of claim 39, wherein said system uses multi-slit scanning technology and overlapping part images are obtained from different slits in said system.

45. The system of claim 39, comprising means for computing said image parameters from comparative analysis with respect to alignment, and comparison of data derived from essentially different sets of part images.

46. The system of claim 45, wherein calculation of said image parameters involves estimation of motion vectors, components of motion vectors or cost functions of parameters for displacement.

47. The system of claim 45, wherein said comparative analysis comprises computing statistics of dissimilarity due to motions.

48. The system of claim 39, comprising a presentation device for presenting said indication as a message suggesting that image quality should be reviewed and/or image should be retaken.

49. A digital x-ray mammography system comprising an x-ray source, a detector and means for receiving an object to be examined, said detector being arranged to produce a signal corresponding to the exposure of said object to x-rays passing through said object, and means for generating a mammogram image data and acquisition of a set of substantially overlapping mammogram part images by scanning an examination field using a bundle of x-ray beams from said x-ray source, an arrangement for fine-alignment of said overlapping mammogram part images based on contents of said mammogram part images, and an arrangement for constructing a resultant image based on said mammogram part images.

50. An arrangement in a digital x-ray mammography apparatus for image correction, the arrangement comprising a displacement estimator, displace/warp units and an image merger.

51. The arrangement of claim 50, wherein said image merger is a mean value calculator.

52. The arrangement of claim 50, wherein said x-ray apparatus is of multi-slit type and said displacement estimator and controller is arranged to receive image data from a detector for each slit and estimate the displacement based on comparison of part images to each other or to a reference image derived from multiple part images.

53. The arrangement of claim 50, comprising an arrangement comprising a threshold for motion detection, which computes an overall figure of merit of estimated motions and compares to a pre-defined threshold value.

54. The arrangement of claim 50, wherein said wherein said estimator comprises instructions for estimation of motion vectors, said instructions being at least one of:
   a. a block matching algorithms that search for maximum correlation/similarity or minimal difference of relatively displaced blocks;
   b. instructions for finding correspondence for selected features, such as corners or edges;
   c. gradient algorithms for optical flow, that use derivatives of the image in spatial and temporal directions to locally estimate one component of the motion vector;
   d. phase from Gabor filters, or quadrature Filters, or Fourier transforms; and
   e. parametric motion models or finite element methods.

55. A computer program stored on a memory for digital x-ray mammography image acquisition by means of an X-ray system, the computer program comprising:
   a. an instruction set for acquiring multi-slit image data by irradiating an object;
   b. an instruction set for automatically analyzing said acquired image data with respect to presence of motion blur; and
   c. an instruction set for indicating whether motion blur is present.

56. A computer program stored on a memory for digital x-ray mammography acquisition comprising:
   a. an instruction set for acquiring image data by irradiating an object using a bundle of x-ray beams that scan an examination area containing said object;
   b. an instruction set for producing a set of overlapping part images;
   c. an instruction set for analyzing said overlapping part images with respect to motions; and
   d. an instruction set for indicating whether motions, or motion blur is present.

57. A computer program stored on a memory for digital mammography x-ray image acquisition comprising:
   a. an instruction set for acquisition of a set of substantially overlapping mammogram part images by scanning an examination field using a set of x-ray beams arranged in a bundle;
   b. an instruction set for fine-alignment of said overlapping mammogram part images based on contents of said mammogram part images; and
   c. instructions for construction of a resultant image based on said mammogram part images.

* * * * *